US00PP14915P2

(12) United States Plant Patent
Zary

(10) Patent No.: US PP14,915 P2
(45) Date of Patent: Jun. 15, 2004

(54) HYBRID TEA ROSE PLANT NAMED 'JACADNOF'

(50) Latin Name: *Rosa hybrida*
Varietal Denomination: JACadnof

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 10/300,570

(22) Filed: Nov. 19, 2002

(51) Int. Cl.[7] ..... A01H 5/00
(52) U.S. Cl. ..... Plt./134
(58) Field of Search ..... Plt./134, 130

*Primary Examiner*—Anne Marie Grunberg
*Assistant Examiner*—June Hwu
(74) *Attorney, Agent, or Firm*—Klarquist Sparkman LLP

(57) ABSTRACT

Hybrid tea rose plant having deep yellow flower color; strong citrus fragrance; deep green, glossy foliage; good resistance to rust and powdery mildew; and long cutting stems.

1 Drawing Sheet

Genus and species: *Rosa hybrida*
Variety Denomination: 'JACadnof'

SUMMARY OF THE INVENTION

The present invention relates to a new and distinct variety of hybrid tea rose plant named 'JACadnof' which was originated by me by crossing the variety 'JACyes,' U.S. Plant Pat. No. 9,390, with an unnamed seedling.

BACKGROUND OF THE INVENTION

The primary objective of this breeding was to produce a new rose variety having the bright yellow, non-fading flower color of the female parent combined with the long flower bud and the dark, glossy, disease resistant foliage of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Deep yellow flower color;
2. Strong citrus (lemon) fragrance;
3. Deep green, glossy foliage;
4. Good resistance to rust and powdery mildew; and
5. Long cutting stems.

Asexual reproduction of this new variety by budding, as performed at Wasco, Calif., shows that the foregoing and all other characteristics and distinctions come true to form and are established and transmitted through succeeding propagations.

COMPARISON WITH PARENTS

'JACadnof' has a longer bud and much greater fragrance than the female parent 'JACyes' and has a deeper yellow flower color than its male parent.

COMPARISON WITH SIMILAR VARIETY

The closest similar variety is the female parent 'JACyes' On both 'JACyes' and 'JACadnof' the flower petals on their upper surface are Yellow Group 13B, but the lower petal surface on the 'JACadnof' petals is Yellow Group 9C whereas the lower surface of the 'JACyes' petals is Yellow Group 13A. Also, the 'JACadnof' mature plant is about 170 cm. in height as compared to the 120 cm height of 'JACyes,' both plants having a width of about 100 cm.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—'JACyes' (U.S. Plant Pat. No. 9,390).
*Pollen parent.*—Unnamed seedling.

FLOWER

Observations made from plants beginning at 3 years of age grown in a garden environment at Somis, Calif. May 2001–May 2002.

Blooming Habit: Continuous.
Bud:
*Size.*—About 5 cm long when the petals start to unfurl.
*Form.*—The bud form is long and pointed ovoid.
*Color.*—When sepals first divide, bud color is Yellow Group 13A. When half blown, the upper sides of the petals are Yellow Group 13B; and the lower sides of the petals are Yellow Group 9C.

*Sepals.*—Color: Upper surface: Green Group 138B. Lower surface: Green Group 143B with prominent midrib of Yellow-Green Group 144C. Length: 40 mm. Width: 15 mm. Shape: Subulate. Surface texture: Upper surface: Hoary. Lower surface: Glandular. There are three heavily appendaged sepals. There are two unappendaged sepals with hairy edges.

*Receptacle.*—Color: Green Group 137C. Shape: Funnel. Size: Large, about 5 mm long×12 mm wide. Surface: Smooth.

*Peduncle.*—Length: Medium, averaging about 8 cm. Surface: Smooth. Color: Green Group 137D but often with a cast of Greyed-Red Group 178C in areas exposed to bright sunlight. Strength: Stiff, erect and heavy.

Bloom:

*Size.*—Large. Average open diameter is about 12–14 cm.

*Borne.*—Singly.

*Stems.*—Strength: Strong. Length: Average length is about 40–60 cm.

*Form.*—When first open: High, centered. Permanence: All petals curl.

*Petalage.*—Number of petals under normal conditions: 25–30.

*Color.*—The upper sides of the petals are Yellow Group 13B. The reverse sides of the petals are Yellow Group 9C. The base of each petal lightens to Yellow Group 9A. The major color on the upper side is Yellow Group 13B.

*Variegations.*—None.

*Discoloration.*—The general tonality at the end of the first day: Yellow Group 13B. At the end of the third day: Yellow Group 13B. By day 5 or 6 there is a fading to Yellow Group 8C then on day 6 or 7 fades to Yellow Group 8D. Petals then drop.

*Fragrance.*—Strong. Character of fragrance: Lemon.

Petals:

*Texture.*—Thick.

*Shape.*—Round to deltoid.

*Size.*—Length: 40 mm. Width: 35 mm.

*Margin.*—Entire. Apex Shape: Obtuse. Base Shape: Cuneate.

*Form.*—Tips slightly recurved.

*Arrangement.*—Imbricated.

*Petaloids.*—Number 5. Color: Yellow Group 15B. Size: Length: 5–8 mm. Width: 4–5 mm. Shape: Oblong to oblanceolate.

*Persistence.*—Petals drop off cleanly before drying.

*Lastingness.*—On the plant: Fair (about 5 days). As a cut flower: Fair (about 7 days).

Reproductive parts:

*Stamens.*—Number: 130–150. Length: 12–16 mm. Anthers: Length 2–3 mm. Color: Yellow Group 12C. Arrangement: Regular around styles. Filaments: Color: Yellow Group 12A. Length: 10–14 mm. Pollen: Color: Yellow-Orange Group 20C.

*Pistils.*—Number: 80–100. Styles: Color: Yellow Group 2C. Length: 10–12 mm. Stigmas: Color: Yellow Group 11B. Length: 1 mm.

*Hips.*—None observed.

PLANT

*Form.*—Bush.

*Growth.*—Very vigorous, upright and branching.

*Age to maturity.*—Two years.

*Mature plant.*—Height: 1.8 m. Width: 1 m.

*Rootstock.*—Dr. Huey.

Foliage: Number of leaflets on normal mid-stem leaves: 5–7.

*Size.*—Large (13–15 cm long×10–12 cm wide).

*Quantity.*—Abundant.

*Color.*—New foliage: Upper side: Greyed-Red Group 178B. Lower side: Greyed-Red Group 178B. Old foliage: Upper side: Green Group 136A. Lower side: Yellow-Green Group 147C.

Leaflets:

*Size.*—About 4–6 cm long×2.5–3.5 cm wide.

*Shape.*—Broadly oval.

*Base shape.*—Rounded.

*Apex shape.*—Acuminate.

*Texture.*—Lustrous and coriaceous.

*Egde.*—Serrated.

*Serrations.*—Single, small.

*Petiole.*—Color: Yellow-Green Group 144B.

*Petiole rachis.*—Color: Yellow-Green Group 144B. Underside: With prickles.

*Stipules.*—Length: 1–2 cm (bearded and edged in glands.) Color: Upper Surface: Green Group 136A. Lower Surface: Yellow-Green Group 147C. Shape: Adnate with middle narrowing downward; margin comb-shaped.

*Disease resistance.*—Resistant to mildew and rust and susceptible to blackspot under normal growing conditions.

*Pest resistance.*—Not tested.

*Vein color.*—Yellow-Green Group 144B.

*Venation pattern.*—Reticulate.

Wood:

*New wood.*—Color: Green Group 137C. Bark: Smooth.

*Old wood.*—Color: Green Group 137B but often the new canes turn Red-Purple Group 183B before becoming green (they go from green to purple to green). Bark Smooth.

Prickles:

*Quantity.*—On main canes from base: Ordinary. On laterals from main canes: 12 per 10 cm length.

*Form.*—Hooked downward.

*Length.*—12 mm.

*Color when young.*—Greyed-Purple Group 183D becoming lighter at the tips-close to Greyed-Red Group 179B then 179C.

*Color when mature.*—Greyed-Orange Group 165A.

Small Prickles:

*Quantity.*—On main stalks: None. On laterals: Few.

*Color.*—Greyed-Purple Group 183D becoming eventually Greyed-Orange Group 165D.

*Size.*—Length: 1–3 mm.

*Shape.*—Needle to hooked slightly downwardly.

Winter Hardiness: Hardy to Zone 5.

What is claimed is:

1. A new and distinct variety of rose plant of the hybrid tea class, substantially as herein shown and described, characterized particularly by its deep yellow flower color; strong citrus fragrance; deep green, glossy foliage; good resistance to rust and powdery mildew; and long cutting stems.

* * * * *

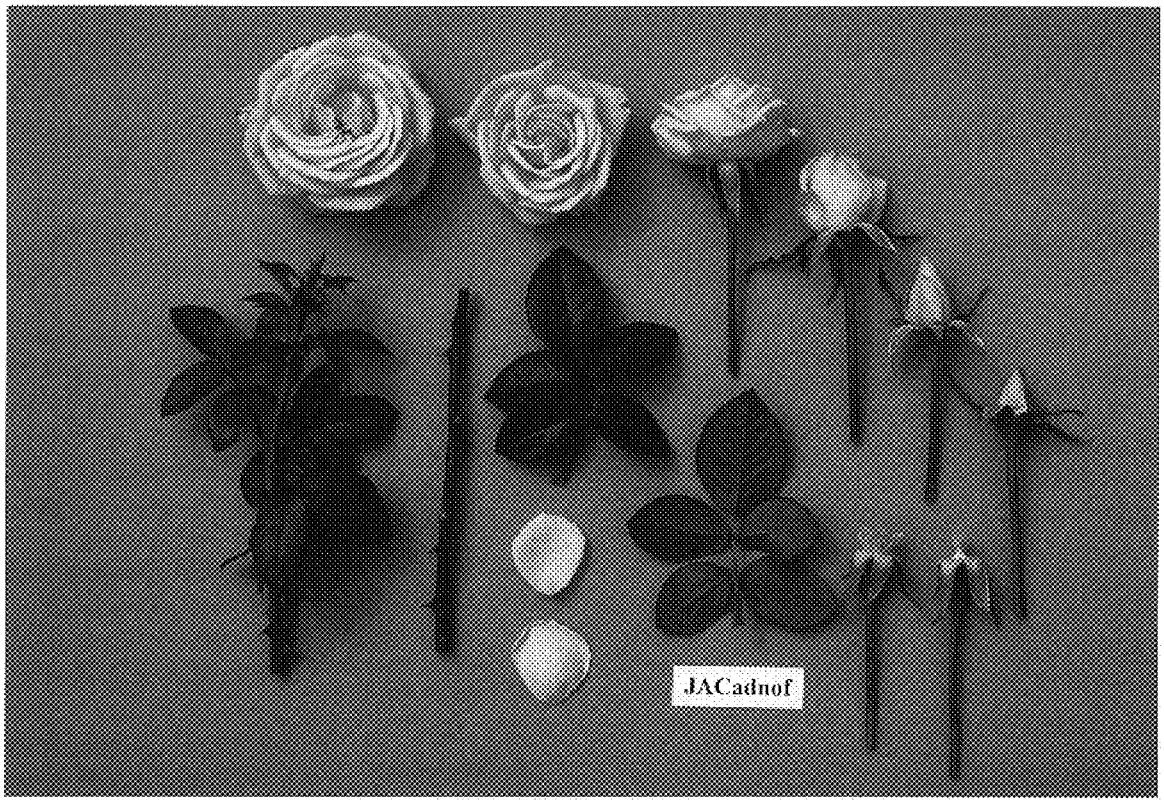
JACadnof